US009061990B2

(12) United States Patent
Mu

(10) Patent No.: US 9,061,990 B2
(45) Date of Patent: Jun. 23, 2015

(54) FLUORINATION OF ACRYLATE ESTERS AND DERIVATIVES

(75) Inventor: YongQi Mu, Los Altos, CA (US)

(73) Assignee: Relypsa, Inc., Redwood City, CA (US)

( * ) Notice: Subject to any disclaimer, the term of this patent is extended or adjusted under 35 U.S.C. 154(b) by 0 days.

(21) Appl. No.: 14/128,899

(22) PCT Filed: Jun. 27, 2012

(86) PCT No.: PCT/US2012/044455
§ 371 (c)(1),
(2), (4) Date: Feb. 4, 2014

(87) PCT Pub. No.: WO2013/003495
PCT Pub. Date: Jan. 3, 2013

(65) Prior Publication Data
US 2014/0221681 A1    Aug. 7, 2014

Related U.S. Application Data

(60) Provisional application No. 61/501,567, filed on Jun. 27, 2011.

(51) Int. Cl.
*C07C 69/63* (2006.01)
*C07C 67/307* (2006.01)
*C07C 51/363* (2006.01)
*C07C 51/62* (2006.01)

(52) U.S. Cl.
CPC ............. *C07C 67/307* (2013.01); *C07C 51/363* (2013.01); *C07C 51/62* (2013.01)

(58) Field of Classification Search
CPC .................................................... C07C 67/307
See application file for complete search history.

(56) References Cited

U.S. PATENT DOCUMENTS 5,072,030 A * 12/1991 Bielefeldt et al. ............ 560/227
7,304,191 B2   12/2007 Mathieu et al.
7,683,222 B2 *  3/2010 Kaneko et al. ................ 570/161

FOREIGN PATENT DOCUMENTS

DE   39 04 707 A1      8/1990
DE   43 09 276 A1      3/1993
JP   EP 06967191 A1 * 12/1999

OTHER PUBLICATIONS

Solomons, Organic Chemistry, 5th edition, 1992, John Wiley & Sons, Inc., New York, pp. 778-780.*
Rozen et al, Journal of Organic Chemistry, Direct Addition of Elemental Fluorine to Double Bonds, 1986, 51, pp. 3607-3611.*
Conte, L., et al., "Fluorination of Hydrogen-Containing Olefins with Elemental Fluorine," Journal of Fluorine Chemistry, 1988, pp. 319-326, vol. 38.
Gassen, K. R., et al., "Synthesis of Alpha-Fluoroacrylic Acid and Derivatives," Journal of Fluorine Chemistry, 1991, pp. 149-162, vol. 55.
Gatenyo, J., et al., "Direct Addition of Fluorine to Arylacetylenes," Journal of Fluorine Chemistry, 2009, pp. 332-335, vol. 130.
Henne, A. L., et al., "Ionization Constants of Fluorinated Acids. III. Unsaturated Acids," Journal of the American Chemical Society, 1954, pp. 479-481, vol. 76, No. 2.
Hutchinson, J., et al., "Elemental Fluorine in Organic Chemistry," Topics in Current Chemistry, 1997, pp. 1-43, vol. 193.
Kamaya, H., et al., "An Efficient Method for Alpha-Monofluorination of Carbonyl Compounds with Molecular Fluorine: Use of Alpha-Hydroxymethylene Substituent as Directing and Activating Groups," Tetrahedron Letters, 1997, pp. 587-590, vol. 38, No. 4.
Kartashov, A. V., et al., "Reactions of Halogen Fluorides XII. Reaction of Bromine Trifluoride with Bromine-Containing Esters. A New Method for the Synthesis of Fluoroalkyl 2-Fluoroacrylates," Translated from Zhurnal Organicheskoi Khimii, 1991, pp. 2522-2528, vol. 27, No. 12.
Merritt, R. F., et al., "Direct Fluorination of Steroidal Olefins to cis-Vicinal Difluorides," Communications to the Editor, Journal of the American Chemical Society, 1966, pp. 1822-1823, vol. 88, No. 8.
Rozen, S., et al., "Direct Addition of Elemental Fluorine to Double Bonds," The Journal of Organic Chemistry, 1986, pp. 3607-3611, vol. 51.
Sandford, G., et al., "Speciality Chemicals from Selective Direct Fluorination," Speciality Chemicals Magazine, May 2002, pp. 35-37.
Sato, M., et al., "A Facile Synthesis of Alpha,Beta-Difluoro-Alpha,Beta-Unsaturated Carbonyl Compounds by Use of Molecular Fluorine Addition," Tetrahedron Letters, 1995, pp. 6705-6708, vol. 36, No. 37.

* cited by examiner

*Primary Examiner* — Paul A Zucker
(74) *Attorney, Agent, or Firm* — Senniger Powers LLP

(57) ABSTRACT

The present invention generally relates to processes for converting acrylate esters or a derivative thereof to difluoropropionic acid or a derivative thereof. This process is generally performed using fluorine gas in a hydrofluorocarbon solvent.

13 Claims, No Drawings

FLUORINATION OF ACRYLATE ESTERS AND DERIVATIVES

FIELD OF THE INVENTION

The present invention generally relates to processes for converting an acrylate ester or a derivative thereof to the corresponding difluoropropionate or a derivative thereof. The process is generally performed using fluorine gas in a hydrofluorocarbon solvent.

BACKGROUND OF THE INVENTION

Potassium ($K^+$) is one of the most abundant intracellular cations. Potassium homeostasis is maintained predominantly through the regulation of renal excretion. Various medical conditions, such as decreased renal function, genitourinary disease, cancer, severe diabetes mellitus, congestive heart failure and/or the treatment of these conditions can lead to or predispose patients to hyperkalemia. Hyperkalemia can be treated with various cation exchange polymers including polyfluoroacrylic acid (polyFAA) as disclosed in WO 2005/097081, WO 2010/022381, WO 2010/022382, and WO 2010/022383, each of which is incorporated herein by reference in their entirety.

Polyfluoroacrylic acid can be prepared by polymerization of alpha-fluoroacrylate esters and derivatives thereof. Although there are several methods known for manufacturing the alpha-fluoroacrylic acid or alpha-fluoroacrylate monomer, many of these potential routes of synthesis are not commercially reasonable due to over-fluorination or the costs of the starting materials. It has now been discovered that certain process conditions for the direct fluorination of an acrylate ester or a derivative thereof using fluorine gas, followed by elimination of hydrogen fluoride, provides the desired alpha-fluoroacrylic acid or alpha-fluoroacrylate monomer in a commercially efficient and cost effective manner.

SUMMARY OF THE INVENTION

The present invention provides a process for fluorination of acrylate esters or a derivative thereof to form a difluoropropionic acid or derivative thereof.

One of the many aspects of the invention is a process for fluorinating a double bond that comprises forming a reaction mixture comprising a hydrofluorocarbon solvent, fluorine gas, and a compound of formula 1

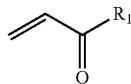

to form a compound of formula 2 in a yield of at least 50%

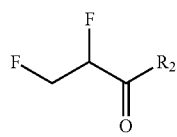

wherein $R_1$ is hydroxy, alkoxy, chloro, or —OC(O)CH=CH$_2$ and $R_2$ is hydroxy, alkoxy, chloro, or —OC(O)CHFCH$_2$F.

Another aspect is a process for fluorinating a double bond that comprises forming a reaction mixture comprising a hydrofluorocarbon solvent, fluorine gas, and a compound of formula 5

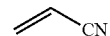

to form a compound of formula 6

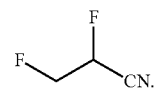

DESCRIPTION OF THE PREFERRED EMBODIMENTS

Fluorination can be difficult to control and can easily result in products that are over fluorinated. Thus, in order to maximize the yield of desired product and minimize side reactions, the solvent, reaction temperature, and additives have been found to be significant. It has been found that fluorination of a double bond (e.g., in compounds such as acrylate esters or derivatives thereof) followed by elimination of hydrogen fluoride is a commercially feasible process for producing alpha-fluoroacrylate ester.

The process for fluorinating a double bond comprises forming a reaction mixture comprising a hydrofluorocarbon solvent, fluorine gas, and a compound comprising a double bond. The compound comprising a double bond can be a compound of formula 1

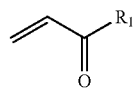

wherein $R_1$ is hydroxy, alkoxy, chloro, or —OC(O)CH=CH$_2$. The fluorination process produces the product compound of formula 2

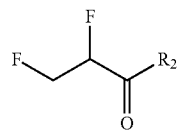

wherein $R_2$ is hydroxy, alkoxy, chloro, or —OC(O)CHFCH$_2$F.

$R_1$ and $R_2$ include, but are not limited to, hydroxy, alkoxy such as methoxy, ethoxy, propoxy, 2-propoxy, n-butoxy, iso-butoxy, sec-butoxy, tert-butoxy, n-pentoxy, iso-pentoxy, sec-pentoxy, or tert-pentoxy, or chloro. Preferably, $R_1$ and $R_2$ are methoxy, $R_1$ and $R_2$ are hydroxy, or $R_1$ and $R_2$ are chloro.

The compound comprising a double bond can also be a compound of formula 5

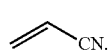

The fluorination process produces the product compound of formula 6

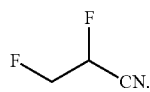

Formula 6

The reaction mixture also comprises fluorine gas. Fluorine gas is generally used in a mixture with an inert gas. Examples of such inert gases are nitrogen and helium. The fluorine/inert gas mixture can contain 1 to 50 mol % of fluorine; about 20 mol % to about 30 mol % of fluorine is preferred.

The reaction mixture also comprises a hydrofluorocarbon solvent. The hydrofluorocarbon solvent comprises 2H,3H-decafluoropentane, eicosafluorononane, tetradecafluorohexane, tetradecafluoro-2-methylpentane, hexafluorobenzene, octadecafluorodecahydronaphthalene, octadecafluorooctane, octafluorocyclopentene, octafluorotoluene, perfluoro(1,3-dimethylcyclohexane), perfluoroheptane, perfluoro(2-butyltetrahydrofuran), perfluorotriethylamine, heptacosafluorotributylamine, tetradecafluoromethylcyclohexane, 1,1,1,3,3-pentafluorobutane, or a combination thereof. Preferably, the solvent comprises 2H,3H-decafluoropentane.

The melting point of the reaction mixture is less than about −20° C., preferably less than about −40° C.

The boiling point of the reaction mixture can be more than about 30° C. When the hydrofluorocarbon solvent has a melting point greater than the desired reaction temperature (e.g., −40° C. or −20° C.), another agent can be added to lower the melting point of the reaction mixture to the desired temperature. For example, dichloromethane or alcohols such as methanol or ethanol, and the like can be added to the reaction mixture to reduce the melting point of the reaction mixture.

Also, the reaction mixture can further comprise a fluorination additive. This fluorination additive can comprise an alcohol, an acid, or a combination thereof. When the fluorination additive comprises an alcohol, the alcohol comprises ethanol, methanol, trifluoroethanol, or a combination thereof. When the fluorination additive comprises an acid, the acid comprises triflic acid, trifluoroacetic acid, sulfuric acid, formic acid, acetic acid, or a combination thereof Further, the reaction mixture can comprise a hydrogen fluoride (HF) scavenger. The HF scavenger comprises sodium fluoride, potassium fluoride, cesium fluoride, calcium fluoride, calcium oxide, magnesium oxide, aluminum oxide, or a combination thereof. Preferably, the HF scavenger comprises sodium fluoride.

The flow rate of introduction of elemental fluorine can be from 0.2 mmol/min to 8.3 mmol/min depending on the reaction scale. The flow rate and reaction time are selected to maximize the conversion of (i) the compound of formula 1 to the compound of formula 2 or (ii) the compound of formula 5 to the compound of formula 6 while minimizing side reactions, particularly side reactions producing compounds that are overfluorinated.

The reaction mixture can contain at least about 1 kg, at least about 5 kg, at least about 10 kg, or more of the compound of formula 1 or 5.

The reaction temperature of the process is from about −80° C. to about −20° C. Preferably, the reaction temperature is from about −80° C. to about −60° C.

The fluorination process can also be performed using a continuous fluorination reactor. Generally, a suitable reactor will include an entry point for the fluorine gas, as well as a temperature control apparatus. The reactor can be of an appropriate size for the scale of the continuous fluorination reaction undertaken. A suitable micro-reactor is shown in Chambers, R. C. et al., "Microreactors for elemental fluorine," *Chem. Commun.*, 1999, 883-884, and the design of such reactor is not considered outside the skill of one of ordinary skill in the art. The reactor can be made of a material that is not reactive with acids, fluorine gas, and other corrosive materials. For example, they can be made of stainless steel, Monel, Hasteloy, and the like.

When carrying out the process described herein using a continuous fluorination reactor, a compound of formula 1 or 5 (e.g., methyl acrylate) is dissolved in a solvent (e.g., 2H,3H-decafluoropentane) at a concentration from about 2 wt. % to about 20 wt. %. This solution is pumped through the reactor at an infusion rate of from about 0.2 mL/minute to about 2 mL/minute. When the reaction is taking place, the reactor is placed on a surface that can be reduced in temperature so that the reactor is at a temperature from about 25° C. to about −80° C. The process can be chilled to about −15° C. At the same time the fluorine gas is passed through the reactor at a gas flow rate of from about 0.2 mmol/minute to about 2 mmol/minute. The compound of formula 1 or 5 and fluorine gas mix inside the reactor, and the product containing the compound of formula 2 or 6 is collected in a receiving flask that is from about 25° C. to about −80° C., preferably, about −78° C.

The fluorine gas can be diluted before addition to the fluorination reactor to about 1% fluorine gas in helium to about 20% fluorine gas in helium.

The residence time of the reactants in the continuous fluorination reactor can be from about 1 millisecond to about 30 minutes. The mean residence time is preferably from about 0.5 seconds to about 1 minute, or more preferably from about 1 second to about 10 seconds.

Without being bound by theory, it is believed that the continuous fluorination reactor provides a shorter contact time between the compound of formula 1 or 5 and the fluorine gas, thus, reducing the over fluorination of the compounds of formula 2 or 6 (e.g., fluorination products).

Once the mixture has reacted to the extent possible to maximize the content of the difluoropropionic acid or derivatives thereof, an esterification or a transesterification reaction can be performed. When derivatives of formula 2 having $R_1$ of hydroxy or chloro are formed, an esterification reaction is performed. When derivatives of formula 2 having $R_1$ of alkoxy is formed, a transesterification reaction can be performed. Each of the reactions can produce the desired alkyl difluoropropanoate by contacting the compound of formula 2 with alcohol and a catalyst. For example, when the methyl difluoropropanoate is desired, methanol is used as the alcohol.

The catalyst for the transesterification can be an acid or a base. When the transesterification catalyst is an acid, it can be a Brønsted acid or Lewis acid. Suitable Brønsted acids include, but are not limited to, toluenesulfonic acid (TsOH), sulfuric acid, hydrochloric acid, phosphoric acid, acetic acid, formic acid, triflic acid, trifluoroacetic acid, or combinations thereof. Suitable Lewis acids include, but are not limited to, boron tribromide, aluminum oxide, titanium tetraethoxide, or combinations thereof.

When the catalyst for transesterification is a base, it can be, for example, dimethylaminopyridine (DMAP), diethylhydroxyamine, triethylamine, N,N-diisopropylethylamine (Hunig's base), pyridine, 1,8-diazabicyclo[5.4.0]undec-7-ene (DBU), 1,4-diazabicyclo[2.2.2]octane (DABCO), or a combination thereof Preferably, the base is dimethylaminopyridine.

For the compound of formula 6, the nitrile group can be transformed to an ester group by reaction with an alcohol and an acid catalyst (i.e., esterification). Preferably, the alcohol is methanol. The acid catalyst can be a Brønsted acid or Lewis acid. Suitable Brønsted acids include, but are not limited to, toluenesulfonic acid (TsOH), sulfuric acid, hydrochloric acid, phosphoric acid, acetic acid, formic acid, triflic acid, trifluoroacetic acid, or combinations thereof. Suitable Lewis acids include, but are not limited to, boron tribromide, aluminum oxide, titanium tetraethoxide, or combinations thereof.

After the esterification or transesterification reaction, the reaction mixture can contain 50 mol %, 55 mol %, 60 mol %, or more of formula 2 (wherein $R_2$ is methoxy) based on the number of moles of formula 1 added to the reaction mixture.

When the continuous fluorination reactor was used, after the esterification or transesterification reaction, the reaction mixture can contain 50 mol %, 55 mol %, 60 mol %, or more of formula 2 (wherein $R_2$ is methoxy) based on the number of moles of formula 1 added to the reaction mixture.

The conversion of the 2,3-difluoropropionic acid or a derivative thereof to α-fluoroacrylate ester or a derivative thereof can be achieved by eliminating HF by addition of a base. Exemplary bases include organic amines such as tertiary amines (e.g., dimethylaniline, trimethylamine, 1,5-diazabicyclo[4,3,0]non-5-ene (DBN) and 1,8-diazabicyclo[5,4,0]undec-7-ene (DBU)), alkoxides, alkali or alkaline-earth hydroxides, or a combination thereof For the elimination of HF, a stoichiometrically equivalent base per mole of a compound of Formulae 2 or 6 is used. Typically, 0.8 to 1.2 equivalents of base are used for elimination of HF.

The elimination of the HF can be carried out, for example, at reaction temperatures from about −78° C. to about 180° C.; preferably, from about −20° C. to about 55° C. Ethers, halogenated hydrocarbons and aromatic solvents can be used as solvents for the elimination of HF reaction.

Unless otherwise indicated, the term "alkoxy," as used herein alone or as part of another group, denotes an —OX radical, wherein X is as defined in connection with the term "alkyl." Exemplary alkoxy moieties include methoxy, ethoxy, propoxy, or 2-propoxy, n-, iso-, or tert-butoxy, and the like.

The alkyl group as described herein is an optionally substituted linear saturated monovalent hydrocarbon radical containing from one to twenty carbon atoms and preferably one to twelve carbon atoms, or an optionally substituted branched saturated monovalent hydrocarbon radical containing three to twenty carbon atoms, and preferably three to eight carbon atoms. Examples of unsubstituted alkyl groups include methyl, ethyl, n-propyl, i-propyl, n-butyl, i-butyl, s-butyl, t-butyl, n-pentyl, i-pentyl, s-pentyl, t-pentyl, and the like.

The term "substituted" as in "substituted alkyl," and the like, means that in the group in question (i.e., the alkyl or other group that follows the term), at least one hydrogen atom bound to a carbon atom is replaced with one or more substituent groups such as hydroxy (—OH), alkylthio, phosphino, amido (—CON($R_A$)($R_B$), wherein $R_A$ and $R_B$ are independently hydrogen, alkyl, or aryl), amino (—N($R_A$)($R_B$), wherein $R_A$ and $R_B$ are independently hydrogen, alkyl, or aryl), halo (fluoro, chloro, bromo, or iodo), silyl, nitro (—NO$_2$), an ether (—OR$_A$ wherein $R_A$ is alkyl or aryl), an ester (—OC(O)R$_A$ wherein $R_A$ is alkyl or aryl), keto (—C(O) R$_A$ wherein $R_A$ is alkyl or aryl), heterocyclo, and the like. When the term "substituted" introduces a list of possible substituted groups, it is intended that the term apply to every member of that group.

Having described the invention in detail, it will be apparent that modifications and variations are possible without departing from the scope of the invention defined in the appended claims.

EXAMPLES

The following non-limiting examples are provided to further illustrate the present invention.

General procedure for fluorination of methyl acrylate. The fluorine line set-up was described in Organic Synthesis, Coll. Vol. 8, p. 286-295 (1993) by Teruo Umemoto, Kyoichi Tomita and Kosuke Kawada. All the work was conducted in an efficient fume hood with a fluorine gas detector in the hood. A cylinder of premixed 20% fluorine in helium was obtained from Matheson Tri-gas, Inc. The reaction was monitored by GC/MS on a DB-5 column.

Example 1

General Procedure for the Synthesis of methyl 2,3-difluoropropanoate (B)

A 100-mL round-bottomed reaction flask was charged with methyl acrylate and solvent. The system was purged with helium. The reaction was chilled to −78° C. in a dry ice/acetone bath. A slow stream of 20% fluorine in helium was introduced to the bottom of the flask under vigorous stirring. The flow rate was adjusted to 47.2 mL/min (0.39 mmol/min) and maintained at this rate while keeping the reaction at −78° C. for 2 hours. The reaction was then purged with helium and warmed to room temperature. Solvent was removed. GC/MS was used to analyze the reaction. When assuming the same response factor for each compound, the product mixture contained 46.8 wt. % of desired product, methyl 2,3-difluoropropanoate (B), along with 4.5 wt. % of starting material (A), 13.8 wt. % of methyl 2,3,3-trifluoropropanoate (D), 11.7 wt. % of fluoromethyl 2,3,3-trifluoropropanoate (E), and 23.2 wt. % of fluoromethyl 2,3-difluoropropanoate (C).

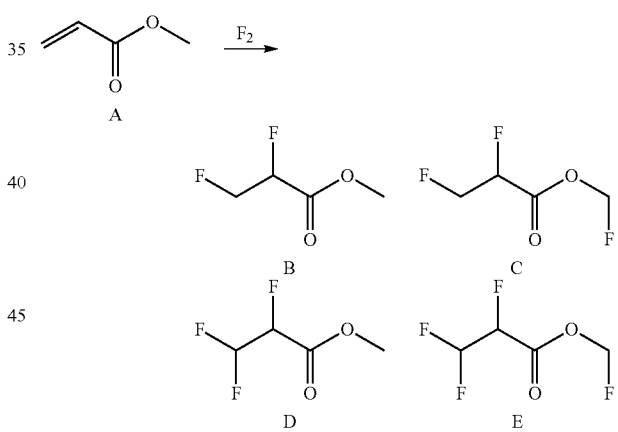

TABLE 1

Experimental conditions using different solvents, temperatures, and fluorine concentrations

| Experiment | Starting material | Amount (mol) | Solvent | | Temp (°C.) | F$_2$ Conc | F$_2$ Equiv. |
|---|---|---|---|---|---|---|---|
| 1 | A | 0.033 | acetonitrile | 50 mL | −15 | 20% | 1.8 |
| 2 | A | 0.022 | acetonitrile | 50 mL | −40 | 20% | 2.3 |
| 3 | A | 0.022 | Dichloromethane | 60 mL | −78 | 20% | 2.1 |
| 4 | A | 0.022 | Pentafluorobutane | 60 mL | −15 | 20% | 2.1 |
| 5 | A | 0.022 | 2H,3H-decafluoropentane | 60 mL | −78 | 20% | 2.1 |

TABLE 1-continued

Experimental conditions using different solvents, temperatures, and fluorine concentrations

| Experiment | Starting material | Amount (mol) | Solvent | | Temp (°C.) | $F_2$ Conc | $F_2$ Equiv. |
|---|---|---|---|---|---|---|---|
| 6 | A | 0.022 | 2H,3H-decafluoropentane | 60 mL | −40 | 20% | 2.1 |
| 7 | A | 0.022 | 2H,3H-decafluoropentane | 60 mL | −78 | 10% | 2.1 |

TABLE 2

Results of using different solvents, temperatures and fluorine concentrations

| Experiment | Product distribution (area %) | | | | |
|---|---|---|---|---|---|
| | A | B | C | D | E |
| 1 | 45.8 | 13.4 | | | |
| 2 | 63.1 | 11.8 | | | |
| 3 | 61.8 | 18.4 | | | |
| 4 | 12.9 | 27.1 | 4.2 | | |
| 5 | 14.9 | 35.5 | 18.4 | 14.5 | 11.5 |
| 6 | 3.1 | 33.6 | 20 | 18.5 | 14.6 |
| 7 | 28.4 | 37.9 | 15 | 11.1 | 7.6 |

TABLE 3

Experimental conditions using different additives and solvent combinations All reactions were conducted at −78° C. using 20% fluorine in helium

| Experiment | Starting material | Amount (mol) | Solvent | | $F_2$ Equiv. |
|---|---|---|---|---|---|
| 8 | A | 0.022 | 2H,3H-decafluoropentane:ethanol | 50 mL:0.1 mL | 2.5 |
| 9 | A | 0.022 | 2H,3H-decafluoropentane:ethanol | 60 mL:1 mL | 2.5 |
| 10 | A | 0.022 | 2H,3H-decafluoropentane:$CF_3SO_3H$ | 50 mL:0.5 mL | 2.5 |
| 11 | A | 0.022 | 2H,3H-decafluoropentane:methanol | 50 mL:5 mL | 2.5 |
| 12 | A | 0.022 | 2H,3H-decafluoropentane:dichloromethane | 30 mL:30 mL | 2.5 |
| 13 | A | 0.022 | 2H,3H-decafluoropentane:2,2,2-trifluoroethanol | 50 mL:1 mL | 2.5 |

TABLE 4

Results from different additives and solvent combinations

| Experiment | Product Distribution (area %) | | | | |
|---|---|---|---|---|---|
| | A | B | C | D | E |
| 8 | 17.7 | 44.1 | 15.8 | 9.73 | 6.1 |
| 9 | 11.4 | 48.5 | 14 | 14.2 | 6.1 |
| 10 | 16.2 | 30.8 | 15.4 | 15.1 | 11.7 |
| 11 | 32.8 | 39.9 | 5.5 | 7.8 | |
| 12 | 27.2 | 13.5 | 1.6 | | |
| 13 | 33 | 37.7 | 11.3 | 9.8 | 6 |

Example 2

Synthesis of 2,3-difluoropropionic acid (G)

To a solution of acrylic acid in 2H,3H-decafluoropentane was added sodium fluoride as scavenger for HF. The suspension was cooled to −78° C. under vigorous stirring. Fluorine was introduced to the mixture under the same conditions as example 1. After the reaction, the mixture was filtered and analyzed by GC/MS.

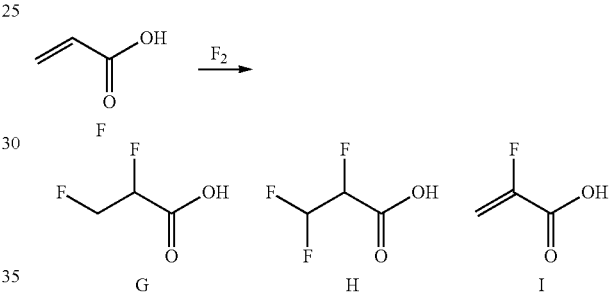

Example 3

Synthesis of methyl 2,3-difluoropropanoate (B) via acryloyl chloride

To a solution of acryloyl chloride in 2H,3H-decafluoropentane was added sodium fluoride as HF scavenger. The suspension was cooled to −78° C. under vigorous stirring. Fluorine was introduced to the mixture under the same conditions described in example 1. After the reaction, the mixture was filtered. Sodium carbonate ($Na_2CO_3$) was added to the filtrate followed by methanol at 0-4° C. The reaction was stirred at room temperature for 2 hours. The mixture was filtered and analyzed by GC/MS.

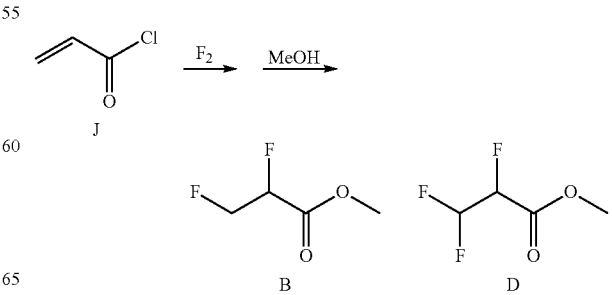

Example 4

Synthesis of 2,3-difluoropropanenitrile (L)

A solution of acrylonitrile in 2H,3H-decafluoropentane was cooled to −78° C. Fluorine was introduced to the mixture under the same conditions described in example 1. After removal of solvent, the mixture was analyzed by GC/MS.

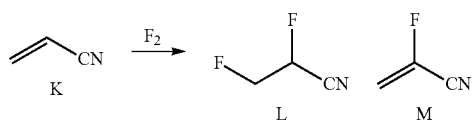

TABLE 5

Experimental conditions of examples 2-4
All reactions were conducted at −78° C. using 20% fluorine in helium

| Experiment | Starting Material | Amount (mol) | Solvent | | $F_2$ Equivalent |
|---|---|---|---|---|---|
| 14 | F | 0.029 | 2H,3H-deca-fluoropentane NaF (2.44 g, 0.058 mol) | 50 mL | 1.6 |
| 15 | J | 0.025 | 2H,3H-deca-fluoropentane NaF (2.1 g, 0.05 mol) | 60 mL | 2.8 |
| 16 | K | 0.0304 | 2H,3H-deca-fluoropentane | 60 mL | 2.3 |

TABLE 6

Results of using different starting materials

| Experiment | Product Distribution (area %) | | | |
|---|---|---|---|---|
| | F | G | H | I |
| 14 | 40.5 | 40 | 10.8 | 5.8 |
| | A | B | D | |
| 15 | 15.2 | 43.5 | 12.5 | |
| | K | L | M | |
| 16 | 38.2 | 24.3 | 10.7 | |

Example 5

Transesterification

To a solution of 2 mL of fluorination reaction mixture was added methanol and a catalyst. The reaction was stirred at room temperature for 48 hours and analyzed by GC/MS.

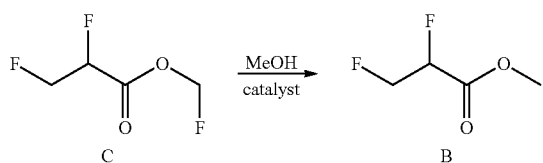

TABLE 7

Results for transesterification

| Experiment | Catalyst | Amount | Product Distribution (area %) | | | | |
|---|---|---|---|---|---|---|---|
| | | | A | E | D | C | B |
| 17 | | | 18.35 | 7.06 | 10.42 | 14.17 | 35.37 |
| 18 | TsOH | 5 mg | 19.75 | 0.00 | 18.42 | 0.37 | 48.23 |
| 19 | DMAP | 10 mg | 19.54 | 0.00 | 18.46 | 1.72 | 46.75 |
| 20 | $H_2SO_4$ (98%) | 50 μL | 19.23 | 0.00 | 17.74 | 0.51 | 47.63 |

To a solution of 2 mL of reaction mixture from direct fluorination was added ROH or methanol and a catalyst. The reaction was stirred at room temperature for 24 hours and analyzed by GC/MS.

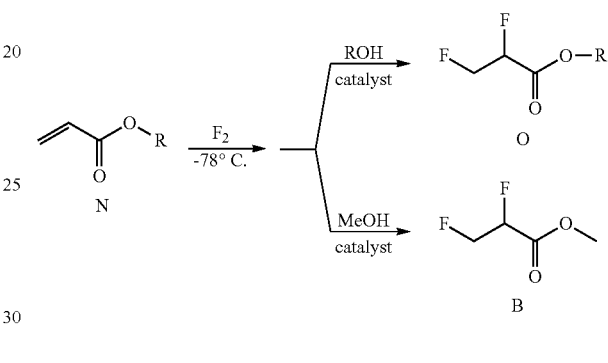

| Experiment | R | ROH | Product Distribution (area %) | | |
|---|---|---|---|---|---|
| | | | N | O | B |
| 21 | Et | EtOH | 41.4 | 39 | |
| | | MeOH | 36.3 | 9 | 43.9 |
| 22 | n-Bu | n-BuOH | 47.1 | 43.7 | |
| | | MeOH | 38.3 | 7.6 | 28.2 |

Example 6

Synthesis of methyl 2,3-difluoropropanoate

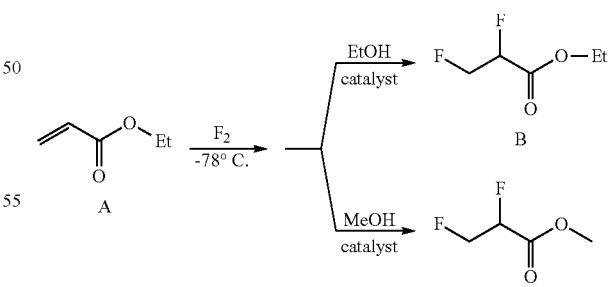

Ethyl acrylate (2 mL) was mixed with 50 mL 2H,3H-Decafluoropentane and cooled in an isopropanol/dry ice bath (−78° C.). The solution was treated with fluorine (20% in helium) at a fluorine flow rate of 0.1 standard cubic feet per hour (SCFH) for 120 minutes. The overfluorinated product ester was trans-esterified by adding methanol or ethanol and DMAP. The conversion was approximately 60%. The difluoro ethyl ester and difluoro methyl ester were observed by Gas Chromatograph-Mass Spec (GCMS).

Example 7

Synthesis of n-butyl 2,3-difluoropropanoate

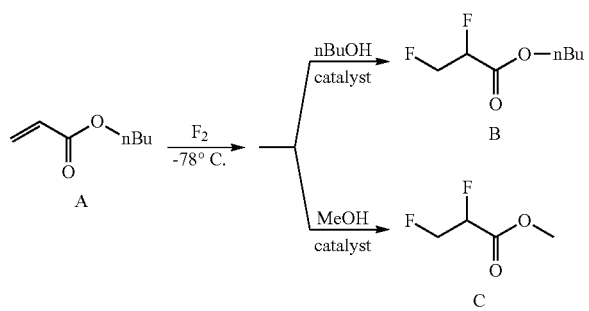

n-Butyl acrylate (2 mL) was mixed with 50 mL 2H,3H-decafluoropentane and cooled in an isopropanol/dry ice bath (−78° C.). The solution was treated with fluorine (20% in helium) at a fluorine flow rate of 0.1 SCFH for 120 minutes. The overfluorinated product was trans esterified by adding methanol and DMAP. The conversion was approximately 40%. n-Butyl 2,3-difluoropropanoate was detected by GCMS.

Example 8

Synthesis of methyl 2,3-difluoropropanoate via t-butyl 2,3-difluoropropanoate

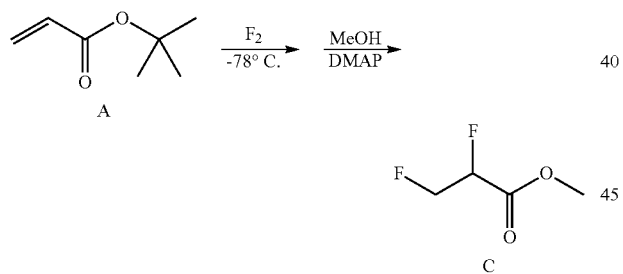

t-Butyl acrylate (2 mL) was mixed with 50 mL 2H,3H-decafluoropentane and cooled in an isoproanol/dry ice bath (−78° C.). The solution was treated with fluorine (20% in helium) at a fluorine flow rate of 0.1 SCFH for 120 minutes. The overfluorinated product ester was trans esterified by adding methanol and DMAP. Gas Chromatography-Mass Spec (GCMS) analysis showed that the starting material was mostly consumed. The mixture was less clean than the methyl acrylate, but the desired product (methyl 2,3-difluoropropanoate) was detected.

Example 9

Continuous Fluorination Process

The continuous fluorination process was tested using a microreactor using a design similar to that in Chambers, R. C. et al., "Microreactors for elemental fluorine," *Chem. Com-*

*mun.*, 1999, 883-884. The methyl acrylate solution was drawn into a 20 mL syringe, and the solution was slowly pumped into the reactor using a syringe pump at a defined rate of addition. The tube for the fluorine gas was connected to a manifold setup that was resistant to corrosion by the fluorine gas. The manifold also allows further dilution of the fluorine gas with helium. The fluorine was supplied as a 20% mixture in helium. The exit stream from the reactor was transfered to a round bottom flask chilled at ~78° C. using an isopropanol/dry ice bath. There was an outlet from the round bottom flask that transfers the reaction atmosphere through a tube that contains Alumina.

Methyl acrylate (1 mL) was dissolved in 2H,3H-decafluoropentane (20 mL) and slowly pumped at 0.7 mL/minute through the reactor. The reactor was placed on a cold surface having a temperature of −15° C. Concurrently, fluorine gas was passed through the reactor at a rate of 0.78 mmol/minute. The two streams mix inside the reactor, react, and were collected in a receiving flask cooled at −78° C. GCMS analysis showed the desired product as the major peaks (7.6 and 7.9 min) as the methyl and fluoromethyl esters. The conversion of reactant was approximately 90%.

In view of the above, it will be seen that the several objects of the invention are achieved and other advantageous results attained.

As various changes could be made in the above methods without departing from the scope of the invention, it is intended that all matter contained in the above description shall be interpreted as illustrative and not in a limiting sense.

The invention claimed is:

1. A process for fluorinating a double bond comprising:
forming a reaction mixture comprising a hydrofluorocarbon or fluorocarbon solvent, fluorine gas, and a compound of formula 1

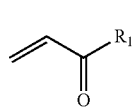

wherein $R_1$ is hydroxy, alkoxy, chloro, or —OC(O)CH=CH$_2$ to form a compound of formula 2 in a yield of at least 50%

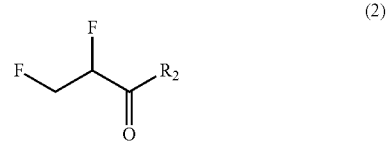

wherein $R_2$ is hydroxy, alkoxy, chloro, —OC(O)CHFCH$_2$F.

2. The process of claim 1 wherein $R_1$ is methoxy.
3. The process of claim 1 wherein $R_1$ is hydroxy.
4. The process of claim 1 wherein $R_1$ is chloro.
5. The process of claim 1 wherein $R_2$ is methoxy.
6. The process of claim 1 wherein the hydrofluorocarbon or fluorocarbon solvent has a melting point less than about −20° C. and a boiling point greater than about 30° C.
7. The process of claim 1 wherein the hydrofluorocarbon or fluorocarbon solvent is 2H,3H-decafluoropentane, eicosafluorononane, tetradecafluorohexane, tetradecafluoro-2-methylpentane, hexafluorobenzene, octadecafluorodecahydronaphthalene, octadecafluorooctane, octafluorocyclopentene, octafluorotoluene, perfluoro(1,3- dimethylcyclohexane), perfluoroheptane, perfluoro(2-butyltetrahydrofuran), perfluorotriethylamine, heptacosafluorotributylamine, tetradecafluoromethylcyclohexane, 1,1,1,3,3-pentafluorobutane, or a combination thereof.

8. The process of claim 7 wherein the hydrofluorocarbon solvent is 2H,3H-decafluoropentane.

9. The process of claim 7 wherein the reaction mixture has a temperature from about −80° C. to about −20° C.

10. The process of claim 1 wherein the reaction mixture further comprises a fluorination additive and the fluorination additive is an alcohol, an acid, or a combination thereof.

11. The process of claim 10 wherein the fluorination additive is the alcohol, and the alcohol comprises ethanol, methanol, trifluoroethanol, or a combination thereof; or the fluorination additive is the acid, and the acid comprises triflic acid, trifluoroacetic acid, sulfuric acid, formic acid, acetic acid, or a combination thereof.

12. The process of claim 1 wherein the process is a continuous process and the infusion rate of the compound of formula 1 is from about 0.2 to about 2 mL/minute.

13. The process of claim 7 further comprising contacting the compound of formula 2 with an alcohol and a catalyst, wherein the catalyst is a Brønsted acid or a Lewis acid.

* * * * *